United States Patent [19]
Roehrig

[11] Patent Number: 5,289,829
[45] Date of Patent: Mar. 1, 1994

[54] LIP-CLOSING ANTI-SNORING DEVICE
[76] Inventor: John A. Roehrig, 252 Pebble Beach Cir., Apt. 101, Naples, Fla. 33962
[21] Appl. No.: 903,287
[22] Filed: Jun. 24, 1992
[51] Int. Cl.$^5$ ............................................. A61F 5/56
[52] U.S. Cl. .................................. 128/848; 602/902; 602/17
[58] Field of Search .............. 128/848, 857, 858, 859, 128/869; 602/18, 17, 19, 902

[56] References Cited

U.S. PATENT DOCUMENTS

| | | | |
|---|---|---|---|
| 2,284,058 | 5/1942 | Kaiser | 602/18 |
| 4,385,627 | 5/1983 | Nelson | 602/17 |
| 4,643,174 | 2/1987 | Horiuchi | 602/18 |
| 4,700,697 | 10/1987 | Mundell | 602/18 |
| 4,782,824 | 11/1988 | Davies | 602/18 |

Primary Examiner—Robert A. Hafer
Assistant Examiner—David J. Kenealy
Attorney, Agent, or Firm—William F. Hamrock

[57] ABSTRACT

The lip-closing, anti-snoring device provides an adjustable, flexible U-shaped device wherein the arcuate shaped base rests on the user's clavical portion of the collar bone and the flexible inverted J-shaped sides are adjusted to lightly embrace and lift the flesh about the chin to maintain the lips in a closed position.

10 Claims, 1 Drawing Sheet

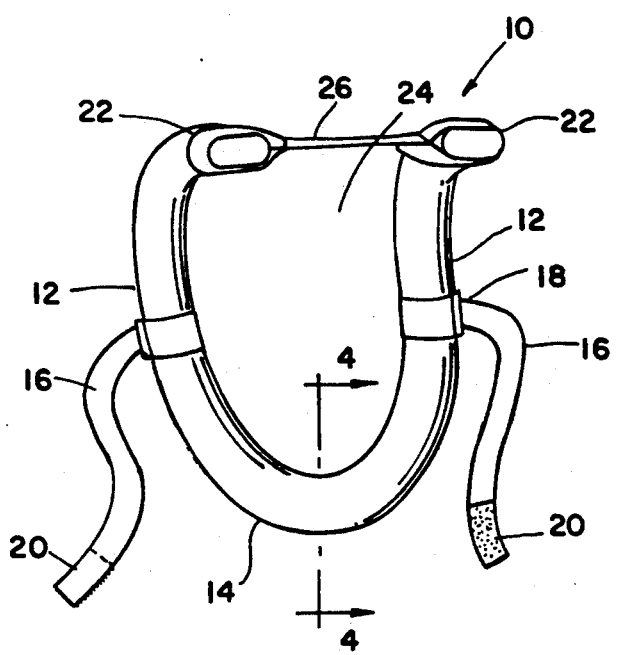
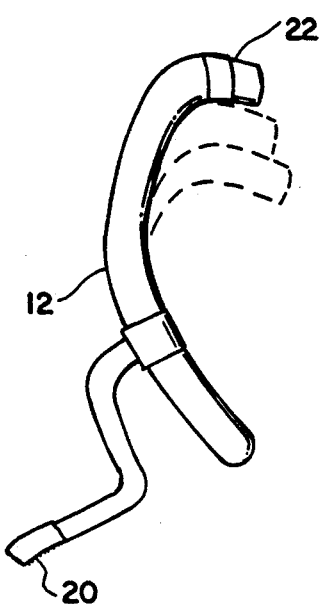
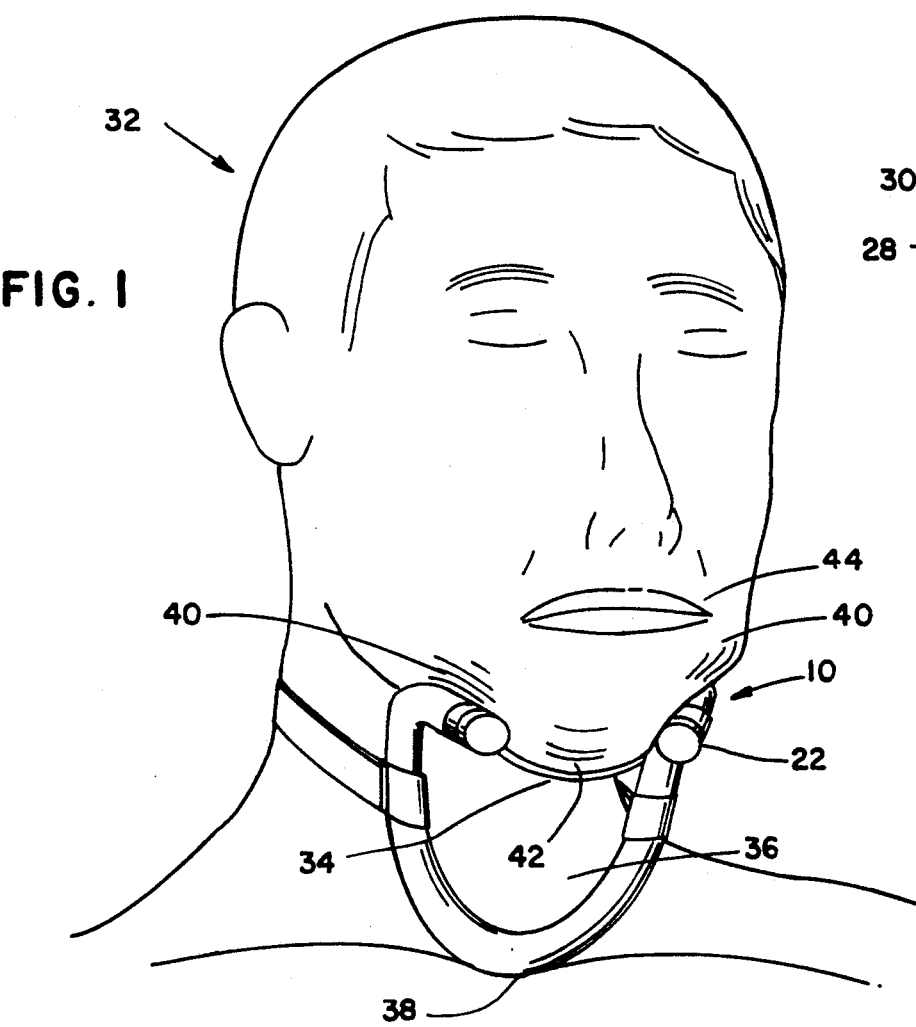
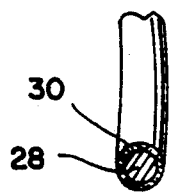

LIP-CLOSING ANTI-SNORING DEVICE

BACKGROUND OF THE INVENTION AND METHOD

1. Field of the Invention

The present invention generally relates to a method and device to prevent snoring and breathing through the mouth, and more particularly, to an adjustable lip-closing anti-snoring device which gently lifts the flesh about the chin area to hold the lips snugly closed.

2. Description of the Prior Art

Various anti-snoring devices directed to maintaining the mouth of a person in a closed position to prevent snoring are known in the prior art. In general, a number of these devices include a harness type fixture designed to fit over the person's head and to cup the chin in a forced upward position thereby causing the mouth to close. Many of these devices exert undue pressure on the jaw and/or are extremely cumbersome and/or are uncomfortable to wear.

U.S. Pat. Nos. 1,990,411 and 3,312,217 appear to be devices which cup the chin in a chin support attached to straps which force the chin in an upward position to hold the mouth in a closed position. U.S. Pat. No. 2,711,730 appears to be for a snoring corrector having a sling of elasticized material having cheek engaging straps which overlie most of the quadrilateral facial area covering the chin to the intersection of the throat with the lower jaw and to the corners of the mouth, to the center of the front side of the ears and passing over the crown of the head, which device is intended to urge upwardly the muscles holding the lower jaw in a closed position and the muscles holding the lower lip in a closed position.

Many of the anti-snoring devices of the prior art are positioned about the person's head and face resulting in uncomfortable pressure being placed upon the face, chin, jaws and/or head. None of the prior art provides an anti-snoring and lip closing method and device which holds the lips in a closed position by gently lifting up the flesh about the chin as herein provided.

SUMMARY OF THE INVENTION

It is an object of the present invention to provide an anti-snoring method of gently lifting up the flesh about the chin which causes the lips to be in a closed position.

It is a further object to provide a device which will gently lift up the flesh about the chin to keep the lips closed.

The lip-closing anti-snoring device of the present invention provides an adjustable U-shaped flesh engaging device. When in use, the base of the U-shaped device rests on the user's clavical portion of the collar bone below the chin and the flexible sides thereof are adjusted to lightly embrace the flesh about the chin and gently lift up the flesh to maintain the lips in a snugly closed position. The method of the invention involves lightly embracing and gently lifting up the flesh about chin thereby closing the lips.

BRIEF DESCRIPTION OF THE DRAWINGS

Although such novel features believed to be characteristic of the invention are pointed out in the claims, the invention and the manner in which it may be carried out may be further understood by reference to the following disclosure and to the accompanying drawings.

FIG. 1 is a frontal view of the head of a user wearing the anti-snoring device.

FIG. 2 is a perspective view of the anti-snoring device.

FIG. 3 is a side view of the anti-snoring device.

FIG. 4 is a cross-sectional view of the device of FIG. 2.

DESCRIPTION OF THE PREFERRED EMBODIMENT

The lip-closing, anti-snoring device in accordance with the present invention is not merely another head and/or face covering, anti-snoring device which puts pressure on the lower jaw or chin to force the mouth in an uncomfortably closed position as in the prior art.

The lip-closing, anti-snoring device disclosed herein is designed and fabricated to lightly raise up the flesh at the sides and under the chin of the user in a gentle upward movement causing the lips to be snugly closed, thus helping to prevent snoring and breathing through the mouth.

A unique feature of the present invention is that the U-shaped device is flexible allowing it to be easily bent to user's features but also to apply the required tension to lift the chin flesh. The result of this feature is that the present lip-closing, anti-snoring device possesses numerous advantages which distinguish it from prior art anti-snoring devices.

By having the U-shaped device prepared from a flexible material, the base and sides thereof can be bent to conform to the user's body features. For example, since the neck and chin areas of users can be different shapes and sizes, the U-shaped device can be bent to conform to these differences making it more comfortable to wear.

A further advantage of the U-shaped device being flexible is that the sides of the device can be adjusted to obtain the individually required tension on the flesh so as to gently lift the chin flesh to close the lips. The U-shaped device is so designed and fabricated that it can be manipulated to snugly fit comfortably within the user's neck area below the chin and into the clavical portion of the collar bone.

Referring to the drawings, and in particular to FIGS. 1 and 2 thereof, the structure and operation of the lip-closing, anti-snoring device 10 of the invention are shown. The purpose of the device is to raise the flesh on the bottom and sides of the chin as seen in FIG. 1. The lips are then snugly closed which helps to prevent not only snoring but also breathing through the mouth as well as drooling. The device works equally well with or without teeth or dentures being present.

More specifically, it will be noted that the preferred embodiment of the anti-snoring device 10 of the invention includes a U-shaped frame formed from a loop of flexible wire or plastic covered with a cushioning material. The loop of wire or plastic is preferably a wire loop formed from 14/2 Romax wire about twelve and one half inches of a generally flattened oval configuration. Other flexible metal, plastic, rubber or similar materials may be used. The cushioning material which covers the loop is preferably a soft cloth material but may be prepared from textiles, rubber or plastic or equivalent material which is comfortable to wear and does not irritate the skin.

The anti-snoring device 10 as seen in FIG. 2 includes a pair of space opposed inverted J-shaped flesh engaging members 12 integrally connected by the clavical engaging arcuate shaped base 14. The inverted J-shaped members 12 are provided with resilient adjustable support straps 16 connected to the lower portion 18 thereof as shown. Support straps 16 fit around the neck of the user and are releasably attached together at their free ends by securing means 20 such as VELCRO or equivalent attaching means to hold the device snugly positioned below the chin.

The pair of inverted i-shaped members 12 extend vertically gradually curving outwardly to approximately a 90° or greater radius bend thereby forming hook members 22. Said hook members lie in a common plane generally perpendicular to the arcuate shaped base 14 and forming opening 24 therebetween. The hook members 22 are connected together by resilient connecting strip 26 which controls the flexible lateral movement of the hook members. Connecting strip 26 is prepared from flexible material similar to that of resilient adjustable support straps 16 except that connecting strip 26 is constructed so that the opening 24 is controlled to be no more than about one and a quarter inches wide or less.

The side view of J-shaped member 12 in FIG. 3 illustrates reforming the J-shaped member bend configurations, shown in phantom, as required to fit the individual outline of the user's features.

Shown in the FIG. 4 in the cross-section view along lines 4—4 of FIG. 2. The flexible wire 28 is shown enclosed within a soft cushioning material 30. The wire 28 is sufficiently resilient to provide an adequate degree of elastic deformation which allows the reforming of the inverted J-shaped member bend configurations to fit the outline of the user's features.

Shown in FIG. 1 is an illustration of a preferred manner of wearing the lip-closing, anti-snoring device 10 of the invention. The device 10 is attached to the user by elevating the head 32 and chin 34 while placing the device 10 within the neck area 36 under the chin with the hooks 22 pointing away from the chin and the arcuate shaped base 14 resting on the user's clavical 38 of the collar bone. The support straps 16 are then fastened snugly around the neck and secured with the attaching means 20 such as VELCRO. Next, the user lowers the head and chin while relaxing the jaw causing the simultaneous gentle elevation of the chin side flesh 40 and chin underside flesh 42. The lifting of the side and underside flesh urges the lips 44 to a comfortable closed position without experiencing excessive pressure.

If initially the pressure exerted on the flesh areas is too great, it is lessened by bending the hooks 22 outwardly and downwardly and/or widening the separation and opening 24 of the inverted J-shaped members 12 from one another by moving them laterally further apart. On the contrary, if initially the pressure exerted on the flesh areas is too weak, it is increased by bending the hooks 22 inwardly and upwardly and/or decreasing the separation and opening 24 of the inverted J-shaped members 12 from one another by moving them laterally closer together.

The lip-closing, anti-snoring device of the invention is designed and constructed to be light-weight and comfortable to wear when in a horizontal sleeping position or even when sitting or standing. It allows the user to sleep comfortably on the back or on either side and permits free rotation of the head when sitting or standing. It prevents the chin from coming in contact with the chest thereby maintaining a clear airway through the trachea. An unobstructed trachea will allow a sleeping user to inspire and expire air without making a snoring sound.

By preventing the chin from coming in contact with chest it would appear that an additional use of the device of the invention would allow clear unobstructed access for the medical insertion of a tube into the trachea of a person having difficulty in breathing.

It will be understood by those skilled in the art that various modifications may be made in device 10 without departing from the spirit and scope of the invention.

What is claimed is:

1. An anti-snoring device for elevating the side flesh and under chin flesh of the chin of a user to maintain the lips in a closed position comprising:

a flexible U-shaped body means having a vertical planar arcuate shaped base member sufficiently structured to fit vertically aligned within the clavicle of the user's collar bone with vertical dual inverted J-shaped members extending upwardly on either side of the vertical arcuate member to the sides of the user's chin, each J-shaped member has a first portion extending in continuous relation with the arcuate shaped base member at an angle less than 30 degrees with respect to the plane containing the arcuate shaped base member, and a second portion extending from and generally perpendicular to the first portion and terminating in a free end, and body securing means extending from each of said J-shaped members, said J-shaped members disposed in adjacent spaced location to one another of sufficient lateral distance to provide each J-shaped member upwardly tensioned contact with the flesh on the side of the chin, said J-shaped members extending upwardly and curving outwardly to form adjustable flexible, upwardly tensioned flesh support means joined together by resilient securing means for said contact with the flesh of each side of the chin.

2. A device according to claim 1 wherein said inverted J-shaped members are integrally joined by said arcuate shaped member.

3. A device according to claim 1 wherein said U-shaped member comprises a resilient core covered with a cushioning material.

4. A device according to claim 3 wherein said resilient core comprises a flexible wire.

5. A device according to claim 4 wherein said cushioning material comprises a soft fabric.

6. A device according to claim 1 said body securing means comprises self-joining, elastic neck strap means.

7. A device according to claim 1 wherein said inverted J-shaped members extending upwardly and outwardly form terminal outward projections joined together by resilient securing means.

8. A device according to claim 7 wherein said resilient securing means comprises an elastic strap.

9. A device according to claim 8 wherein said elastic strap limits said adjacent spaced J-shaped members to be within about one and a quarter inches apart.

10. A device according to claim 2 wherein said arcuate shaped member is sufficiently structured to fit within the clavical of the user's collar bone.

* * * * *